United States Patent [19]

Cook

[11] Patent Number: 5,003,994
[45] Date of Patent: Apr. 2, 1991

[54] ORAL APPLIANCE FOR IMPROVING BREATHING AND METHODS OF USING AND MAKING SAME

[76] Inventor: George W. Cook, P.O. Box 70, Holdingford, Minn. 56340

[21] Appl. No.: 419,076

[22] Filed: Oct. 10, 1989

[51] Int. Cl.⁵ .............................................. A61F 5/56
[52] U.S. Cl. ..................................... 128/848; 128/859; 128/861
[58] Field of Search ............................. 128/846–848, 128/859–862

[56] References Cited

U.S. PATENT DOCUMENTS

| | | | |
|---|---|---|---|
| D. 302,036 | 7/1989 | George | D24/34 |
| 587,358 | 8/1897 | Anderson | 128/861 X |
| 746,869 | 12/1903 | Moulton | 128/861 X |
| 1,674,336 | 6/1928 | King | 128/861 X |
| 2,424,533 | 7/1947 | Faires | 128/861 X |
| 2,574,623 | 11/1951 | Clyde | 128/861 X |
| 2,627,268 | 2/1953 | Leppich | 128/861 X |
| 2,705,006 | 3/1955 | Cettel et al. | 128/861 X |
| 3,132,647 | 5/1964 | Corniello | 128/861 X |
| 3,434,470 | 3/1969 | Strickland | 128/861 X |
| 3,478,742 | 11/1969 | Bohlman | 128/861 X |
| 4,169,473 | 10/1979 | Samelson | 128/861 X |
| 4,196,724 | 4/1980 | Wirt et al. | 128/861 X |
| 4,304,227 | 12/1981 | Samelson | 128/861 X |
| 4,715,368 | 12/1987 | George | 128/136 |
| 4,901,737 | 2/1990 | Toone | 128/848 |

Primary Examiner—Danton D. DeMille
Assistant Examiner—Kerry Owens
Attorney, Agent, or Firm—Henry C. Kovar

[57] ABSTRACT

A new and improved oral appliance for improving breathing, reducing or eliminating snoring, and preventing sleep apnea has a rigid shell with an upper tray, a lower cam structure to advance the mandible structure forward with respect to the maxilla structure, stops to hold the mouth partially open, and a soft resilient pliable socket inside of the tray. The pliable socket has tooth sockets for a plurality of upper teeth, and a gum socket for the maxilla gigiva tissue enabling the pliable socket to conform to the users dental structure and to spread the stress loading to maxilla structure without pain. Methods of using and making the appliance are also provided.

20 Claims, 4 Drawing Sheets

ORAL APPLIANCE FOR IMPROVING BREATHING AND METHODS OF USING AND MAKING SAME

BACKGROUND OF THE INVENTION

1. Field of the Invention

This invention pertains to an improved oral appliance for improving breathing, reducing snoring and preventing apnea, and to methods of improving breathing and making an improved appliance.

2. The Prior Art

A significant fraction of the human pupulation has difficulty breathing when sleeping. The primary manifestations of breathing difficulties during sleep are snoring and sleep apnea.

Snoring is merely a symptom of a respiratory problem which manifests itself during sleep. These respiratory problems if left untreated, pose serious and even life-threatening risks.

The sound associated with snoring is produced when weak loose muscle tissues at the back of the mouth collapse into the pharyngeal airway, blocking normal breathing. Air must then be forced through the passage. That aggravating noise is created by vibrations of the soft muscle tissues as air is forced past them. Snoring is aggravating to family and friends and a cause of considerable interpersonal conflict. Professional and lay people alike realize that elimination of snoring is desirable.

Sleep apnea due to an obstructed airway, is a cause of serious disorders. Some of these disorders which have been frequently seen include daytime sleepiness, nocturnal insomnia, snoring as previously mentioned, abnormal motor activity during sleep, intellectual and personality changes, sexual impotence, morning headaches, systemic hypertension, pulmonary hypertension, COR pulmonale, heart failure, polycythemia, and unexplained nocturnal death.

There are several disorders associated with obstructive sleep apnea. These associative disorders include obesity, adenotonsillor hypertrophy or lymphoma, myxedema, micrognathia, goiter, myotonic dystrophy, temporomandibular joint disease and Shy-Drager syndrome.

Obstructive sleep apnea syndrome (OSAS) is receiving increasing attention as our understanding of these diseases broadens. OSAS is characterized by excessive daytime sleepiness and repeated episodes of upper airway obstruction during sleep.

The etiology of OSAS is unclear, but the sequence of events is established. In spite of normal central nervous system input and thoracic respiratory, effort, closure of the airway begins in the hypopharynx and oropharynx with inspiration. This causes airflow to cease, even though the larynx remains patent. The apneic period and the ensuing hypoxia are broken by cortical awakening and recruitment of accessory muscles. Thus, the person with OSAS will have many awakenings during the night and periods of decreased blood oxygenation.

The diagnosis of OSAS can be made by careful clinical history and overnight investigation in a sleep laboratory. Monitors applied to patients to record information while they sleep and in the morning, the paper recording is analyzed to correlate airway patency with sleep activity.

Treatment of OSAS is individualized, based on the severity of disease and physiological compromise.

Tracheostomy is universally successful, since the obstruction is supraglottic. Some patients experience apneas only when sleeping supine and may be treated with devices to encourage other sleep positions.

Drugs are of limited utility. Uvulopalatopharyngoplasty is successful in approximately 50 percent of people undergoing this procedure. The operation consists of removal of the uvula and redundant tissue in the pharynx. Air under continuous positive pressure may be delivered via a nasal mask during sleep to pneumatically splint the airway open.

The hallmark characteristics of people with OSAS are: overweight, sleepy, adult males.

Through many case reports, it is apparent that a group of people lacking the aforesaid age/sex/weight characteristics of OSAS have the disease. These people's common trait was a retrusive mandible.

The distance from the mandible to the hyoid bone and the diameter of the oropharyngeal airway shadow correlate to the presence of OSAS.

Mandibular lengthening procedures have been utilized in this group to attempt to increase airway diameter by repositioning the submandibular tissue forward. Procedures have included ramus osteotomies, costochondral grafts, and genioplasties. Series with successful utilization of various mandibular surgical procedures in patients with OSAS have been reported.

The night time use of splints to anteriorly reposition the mandible may serve as a predictor of success prior to mandibular advancement. Splints may also be utilized as an interim treatment prior to definitive surgery.

The diagnosis and treatment of OSAS is a field of emerging interest to a wide variety of professionals, including dentists.

Peter T. George in his U.S. Pat. No. 4,715,368 and DES302,036 has provided a discussion of OSAS and the prior art efforts on the subject. George provides an oral appliance that has rigid sockets for both the maxilla and mandible dental structure, a labial arch wire to engage the front superior dental arch, maxillary molar clasps and mandibular molar clasp. While George is silent in his specification as to mandibular advancement, it is obvious and apparent from examination of George's drawings that he has advanced the mandibular structure about one tooth because of George's mandibular clasp (11) being ½ tooth ahead of his maxillary clasp (5). The normal human has the mandibular molar about ½ tooth being or to the rear of the maxillary molar. The George device locks the mandibular and maxilla structures together.

Drs. Thomas E. Meade and Marvin B. Hays of the University of New Mexico have devised, tested and produced an oral appliance for the improvement of breathing during sleep and the prevention of snoring and obstructive apnea. Meade and Hays have sold this device under the trademark "Silent Night."

The Meade and Hays appliance is an integral one-piece device made of rigid cast acrylic and has a upper section which positively and rigidly fits upon the crowns of the upper or superior dental arch. The lower part of the device has a cam and a stop to engage the lower or inferior dental arch and extend the mandible forward to hold the throat airway open. The stop structure spaces the superior and inferior dental arches from each other and breathing apertures are provided.

The Meade and Hays appliance does provide prevention of snoring and obstructive apnea.

However, the Meade and Hays appliance is extremely painful to use. The problem is that the entire Meade and Hays appliance is precisely fitted to the upper crowns and is completely rigid. The force loadings applied by the appliance to the upper teeth are concentrated point loadings and the appliance tends to move the teeth of the user. This device will not conform to the user's dental geometry, so, usage is painful, keeps the user awake, and leaves the user with a very painful mouth in the morning.

OBJECTS OF THE INVENTION

It is an object of this invention to provide a new and improved oral appliance for providing improved breathing, reduction of snoring and reduction of obstructive apnea.

It is an object of this invention to provide a new and improved oral appliance for providing improved breathing during sleep and which is generally painless to use.

It is an object of this invention to provide a new and improved method of improving breathing with an oral appliance.

It is an object of this invention to provide a new and improved method of making an oral appliance for improving breathing.

It is an object of this invention to provide an improved oral appliance made by this new and improved method.

SUMMARY OF THE INVENTION

According to the principles of this invention, an oral appliance for improving breathing has a structural shell with opposed upper and lower sides, lower structure for engaging and advancing mandibular structure, upper structure for engaging maxilla structure and positioning the shell, and the upper structure is soft and pliable as compared to the shell.

An oral appliance for improving breathing during sleep and for reducing snoring has pliable socket structure for conformably engaging one of the maxilla or mandible structures, and outward projecting structure for advancing the mandible forward with respect to the maxilla.

A method of improving breathing has the steps of placing a rigid oral appliance shell in a users mouth and between upper and lower teeth, locating the shell by pliantly engaging maxilla strutures with a soft structure secured to the shell, and advancing the users mandible structure forward with a lower structure on the shell.

A method of making an oral appliance has the steps of making impressions of maxilla and mandible dental structure, casting replicas thereof, making a structural shell between the replicas, making structure on a lower side of the shell for locating the mandible, making upper structure on the shell for engaging the maxilla dental structure, and making the upper structure softer and more pliable than the shell.

An oral appliance for improving breathing, is made by the aforesaid method.

Many other advantages, features and additional objects of the present invention will become manifest to those versed in the art upon making reference to the detailed description and accompanying drawings in which the preferred embodiment incorporating the principles of the present invention is set forth and shown by way of illustrative example.

DESCRIPTION OF THE PREFERRED EMBODIMENT

Figure 1:
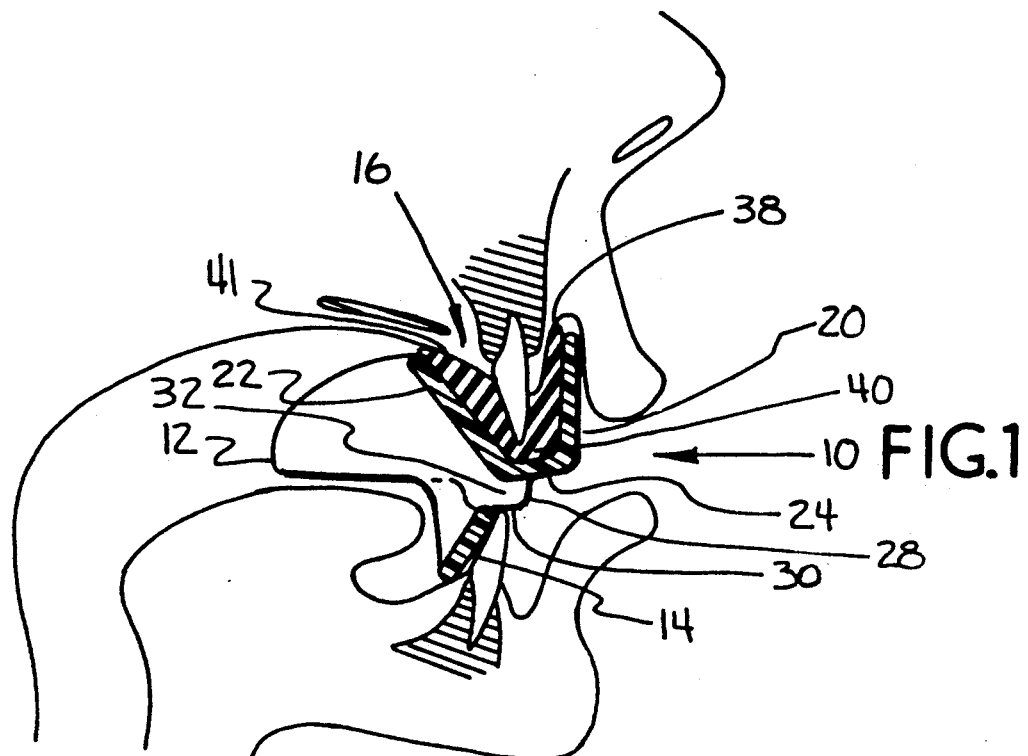
FIG. 1 is an elevational cross sectioned view through a human head, showing the preferred embodiment of the oral appliance of the present invention is use.
Figure 2:
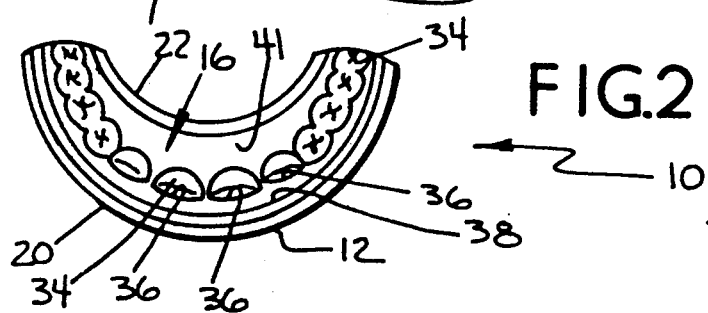
FIG. 2 is a top plan view of the oral appliance of FIG. 1.
Figure 3:
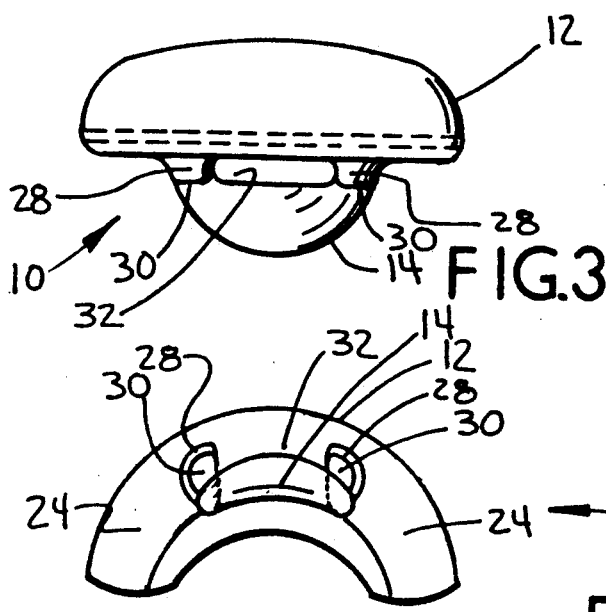
FIG. 3 is a front elevational view projected from FIG. 1.
Figure 5:
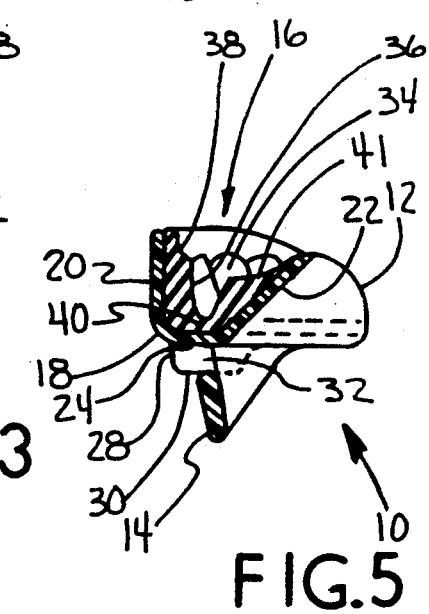
FIG. 5 is a side sectioned view taken through lines V—V in FIG. 3.
Figure 4:
FIG. 4 is a bottom plan view projected from FIG. 3.

An oral or dental appliance for improving breathing, preventing snoring, and preventing apnea is shown in FIGS. 1-5 and generally indicated by the numeral 10.

The appliance 10 has a rigid shell 12, a cam structure 14 and a pliant socket structure 16 for engaging upright portions of dental and gum structure on the top or bottom of the mouth, but preferrably the maxilla or upper dental and gum structure.

The shell 12 has a generally U-shaped cross-section tray 18 that extends arcuately to form a semi-circle within which a plurality of teeth are accepted. The shell 12 and the tray 18 have a front upright 20 that extends upward past the tooth/gum line and which extends upward at least 3 mm (0.12 inch) above the gum line. The upright 20 extends arcuately around the entire outer periphery of the shell 12 and the tray 18 and the upright 20 extends above the gum line for a majority of this arcuate length. The arcuate span of the shell 12 and the upright 20 preferrably encloses at least ten and preferrably twelve maxilla teeth and the gums above these teeth; specifically the shell 12 and upright enclose the central incisor, lateral incisor, canaine, and first and second premolar teeth. An inner upright 22 also arcuately extends the same length as the front upright 20. Between the uprights 20, 22 is a generally horizontal annular plate 24 which is shaped like a segment of an annular flat ring to complete the tray 18. The inner upright 22 also extends upward beyond the gum line at least 3 mm (0.12 inch). It must be emphasized that the shell 12 and tray 18 do not actually touch the maxilla dental or gum structure as will be explained. On the lower side of the annular plate 24 is the cam structure 14 which has a shape that approximates a segment of a truncated cone. At each lateral front corner of the cam 14 is a tooth stop 28 that has a flat shelf 30 in front of the cam 14.

In between the stops 28 is a breathin aperture 32. The entire shell 12 including the uprights 22, 24 and the plate 26 the cam 14 and stops 28 comprise an integral one-piece rigid cast plastic shell 12 that is preferrably made of a castable plastic such as acrylic.

An important feature of this invention is the pliant socket 16 inside of the uprights 20, 22 and plate 24. The pliant socket 10 lines the entire U-shaped section 18 and is the only part of the appliance 10 that makes direct contact with maxilla structure. The pliant socket 16 is preferrably made of a material such as silicone and is softer and more pliable than the shell 12. The pliable socket 16 is permanently bonded to the shell 12 and spaces the upper teeth and gums from the tray 18. The pliant socket 16 has a plurality of tooth sockets 34, each tooth sockets 34 being for a particular maxilla tooth as previously discussed. The tooth sockets 34 are spaced rearward of the front upright 20, forward of the inner upright 22, and upward of the shell plate 24. The pliant socket 16 is preferrably a single piece of soft pliant and resilient material. Each of the tooth sockets 34 has a generally upright soft surface 36 specifically for engaging the complete outer or front surface of the crown of the respective tooth.

Above and to the front or outside of the tooth sockets 34 is an outer upper structure 38 which directly abutts and engages at least 3 mm (0.12 inch) of the gingiva (gum) which is above the tooth/gum line. The outer upper structure 38 abutts against and engages a majority of the gingiva tissue above the teeth to which the pliant socket 16 is fitted. In most people, the upper or maxilla front teeth are spaced forward of the lower or mandible front teeth. The appliance 10 is structured so that when it is in place on the upper teeth, the cam 14 will force the entire mandible structure including teeth, jaw bone, tongue and the front structure in the throat, forward about 6 mm (0.24 inches) when the front lower teeth are abutted against the teeth stops 28. The entire structure of the appliance 10 is structured to hold the upper and lower teeth open about 8 mm (0.32 inch) from closed, which is sufficient to hold the lips open and to permit air flow both in and outward through the breathing aperture 32 and to each side of the cam 14. The cam 14 is configured to comply with the unique configuration of the users lower teeth and the human mandible structure is well adapted to be pulled or pushed forward by the front lower teeth and gums. The reactive force is a rearward vector upon the maxilla structure. The rearward vector or force is spread among the upper teeth and the upper gums and the tooth sockets 34 and front upper structure 38 pliantly and resiliently comply to the physical presence and shape of the maxilla structure, whereas with the prior art the mandible structure had to conform to the rigid structure of a prior art shell that had only rigid partial height tooth sockets that might or might not be identical to the position and disposition of the teeth when the appliance is used.

The entire force to push the mandible structure out is spread uniformly to the rigid maxilla structure through several of the upper teeth and to the maxilla alveolar bone through the upper gangiva (gums) above the engaged teeth. The upward force upon the appliance 10 when the lower teeth abutt the stops 28 is dispersed to the maxilla alveolar bone and the palate bone through the soft inner upper structure 41. This is a new and improved method of improving breathing and is an important aspect of this invention. The human using the new oral appliance 10 can wear the appliance 10 overnight and for extended periods of time without dental pain, without gum abrasions and pain, and without loss of sleep.

A new and unique method has been devised for construction of the oral appliance 10 and is an important further aspect of this invention. The method will be explained and the sequence of steps will be followed in FIGS. 6 through 18.

Figure 6:
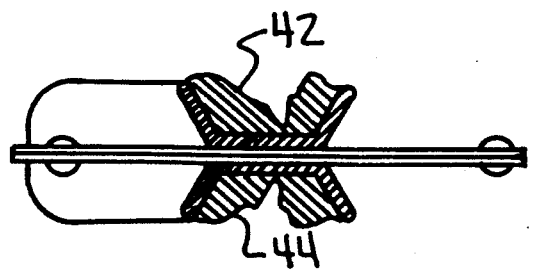
FIG. 6 is a sectioned view of dental impressions.

FIG. 6 shows a double dental impression 42, 44 taken of a future user of an appliance 10. The impressions 42, 44 are taken in appropriate upper and lower impression trays which are fastened together and are registered.

Figure 7:
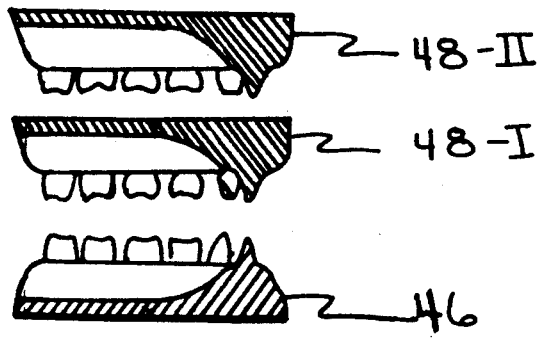
FIG. 7 is a sectioned view of dental replicas.

FIG. 7 shows a single lower dental replica or model 46 cast of lab stone in the lower impression 44 using conventional technique, and two (2) identical upper dental replicas 48-I, 48-II that are cast in the upper impression 42 using conventional dental lab techniques.

Figure 8:
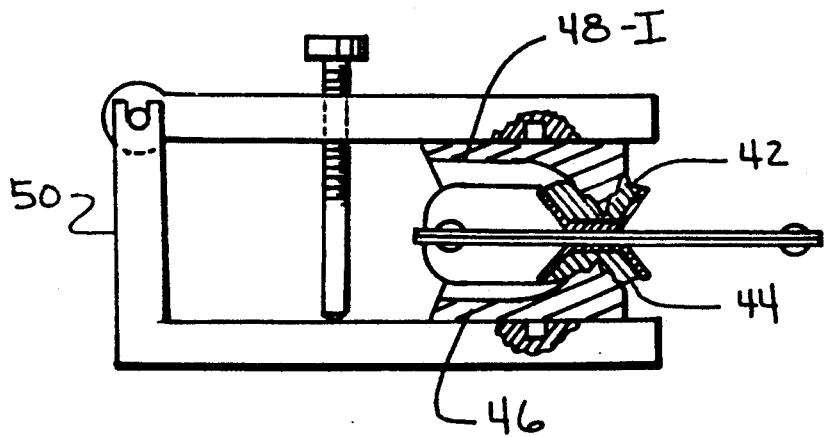
FIG. 8 is a sub elevational view of the impressions and replicas in a first dental articulator.

FIG. 8 shows the lower replica 46 and first upper replica 48-I being mounted in a conventional dental articulator 50 utilizing the upper and lower impressions 42, 44 and the two impression trays as shown in FIG. 6.

Figure 9:
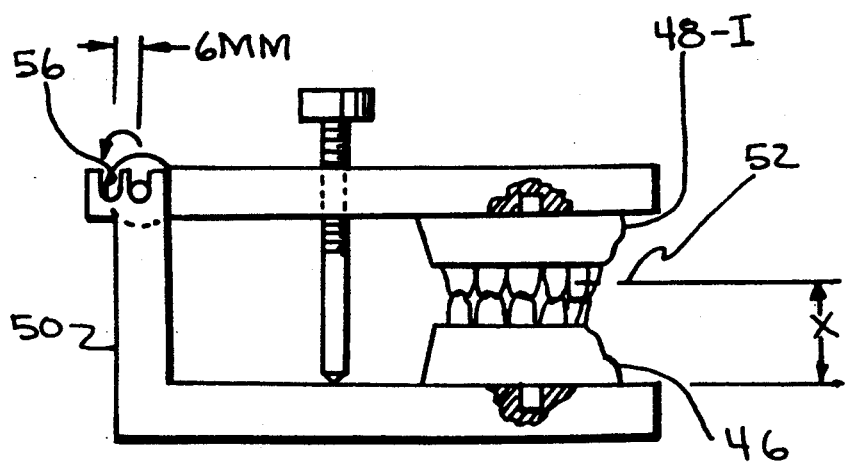
FIG. 9 is a side elevational view of the impressions and replicas in a second dental articulator.

FIG. 9 shows the lower replica 46 and first upper replica 48-I. The replicas 46, 48 are firstly mounted in normal and optimal bite registration and a datum line 52 is scribed on the front of the replicas. The articulator 50 is them adjusted to open up the bite about 8 mm (0.32 inch) using the conventional adjustment device in the articulator 50. The upper jaw 54 of the articulator 50 is then moved rearward about 6 mm (0.24 inch) into a new second fulcrum 56 provided in an otherwise conventional articulator 50. This opening and offset are what is nominally desired in an appliance 10 for an average adult human. Smaller people and unusually large people may require smaller or larger openings and offsets as the case may be.

Figure 10:
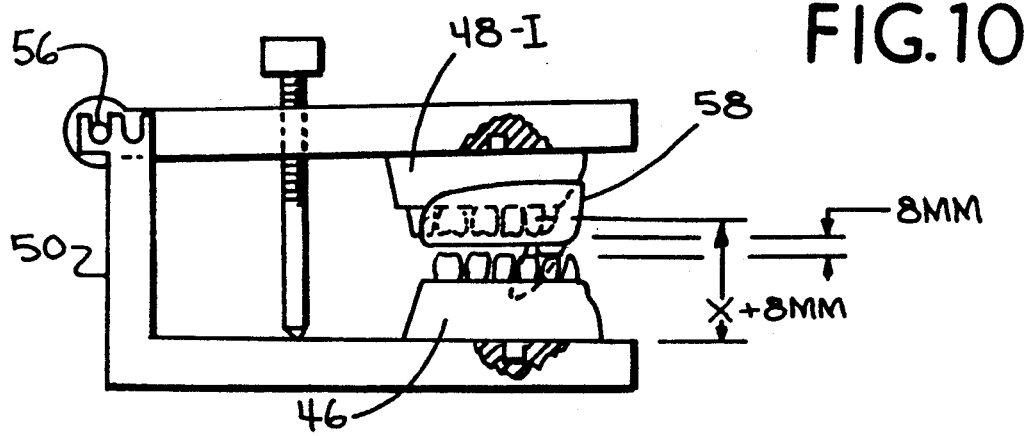
FIG. 10 is a subsequent view of the structure of FIG. 9.

FIG. 10 illustrates a wax-up model 58 of the entire volume of the future appliance 10 formed up on the first upper replica 48-I, using the lab wax sheet normally found and used in dental labs. The wax-up model is manually made upon the first upper replica 48-I utilizing the opening and offset that were provided in the previous step.

Figure 11:
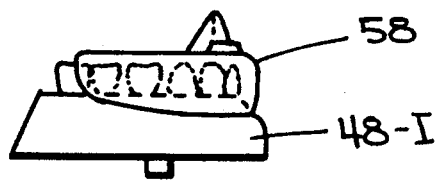
FIG. 11 is a side view of one of the replicas of FIG. 7.

FIG. 11 shows the finished wax model 58 of the appliance 10 on the first upper replica 48-I after removal from the articulator 50. The model 58 is completed with the cam structure 14.

Figure 12:
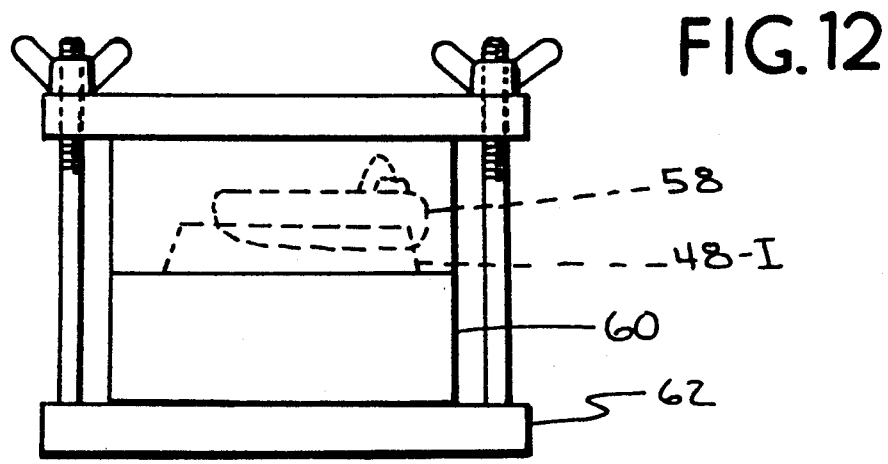
FIG. 12 is a side elevational view of the structure of FIG. 11 in a dental jig and jig blocks.
Figure 13:
FIG. 13 is a side view of the shell for the oral appliance of FIG. 1.

FIG. 12 illustrates the next step wherein the first upper replica 48-I and the wax model 58 are utilized in a conventional lab stone mold set 60 and dental jig 62, to cast a rigid plastic shell casting 64 as shown in FIG. 13 by the conventionally practiced lost wax process. Upon extraction of the shell casting 64 from the mold set 60, the first upper replica 48-I must be destroyed and is therefore also lost.

Figure 14:
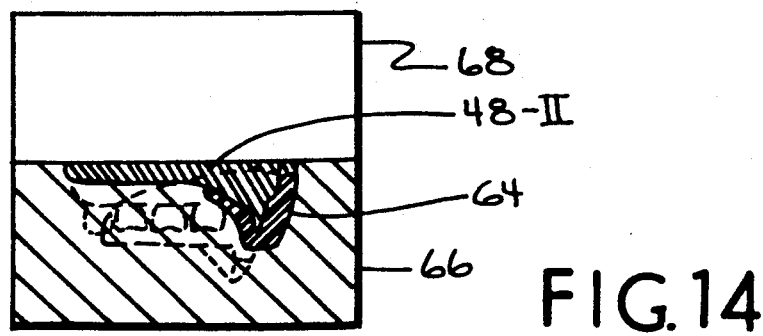
FIG. 14 is a side view of the shell and a replica in jig blocks.
Figure 15:
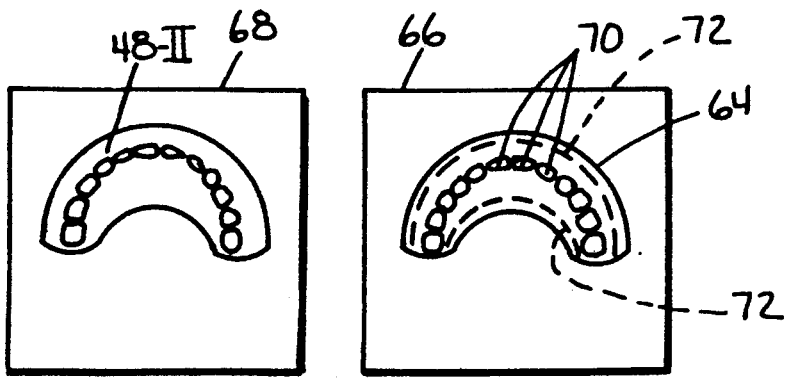
FIG. 15 is a top plan view of the opened structure of FIG. 14.

In the next step shown in FIG. 14, the shell casting 64 is placed in a lower mold 66, and the second replica 48-II is placed in an upper model 68 and is registered into and with the casting tooth sockets 70. Then the mold halves 66, 68 are separated as shown in FIG. 15.

Figure 16:
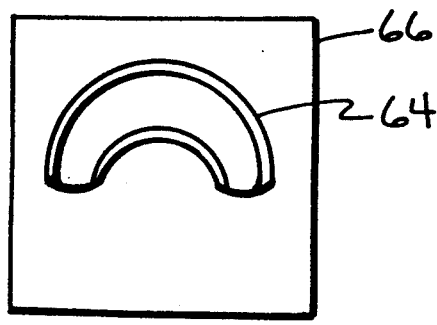
FIG. 16 is a subsequent top plan view of the structure of FIG. 15.

The next step is shown in FIG. 16 wherein the interior material of the shell casting 64 is removed with an appropriate machine tool. Specifically the shell casting 64 has the material definng the casting tooth sockets 70 removed and then further casting material is removed to leave the front upright 20, the inner upright 22, and the plate 24. If you refer back to FIG. 15, the dotted lines designated by the numeral 72 indicate the boundaries of the material to be removed from the shell casting 64.

Figure 17:
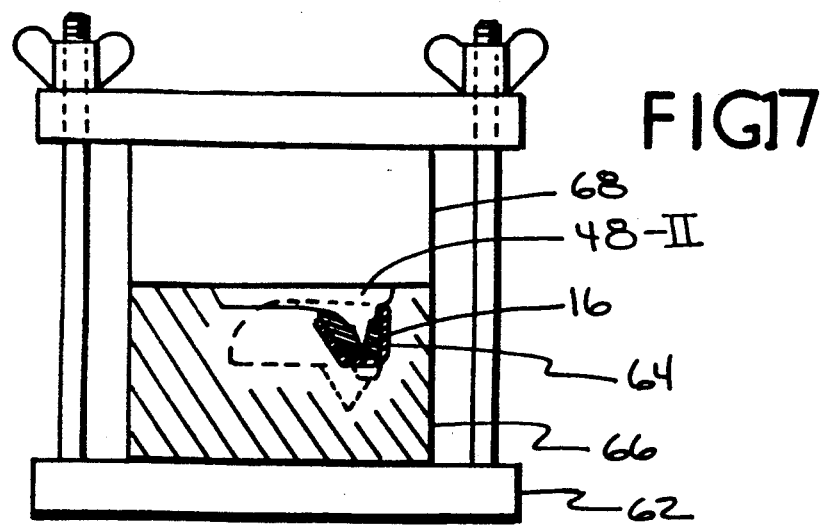
FIG. 17 is a subsequent side plan view of the structure of FIG. 15.
Figure 18:
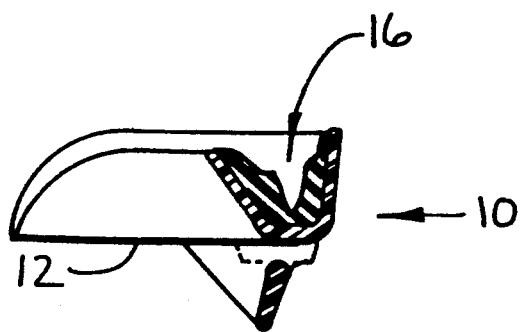
FIG. 18 is the completed casting for the oral appliance of FIG. 1.

In the next step shown in FIG. 17, the hollowed out and voided shell casting 64 is filled with liquid silicone. The lower and upper molds 66, 68 are registered and clamped together in the dental jig 62. The silicone is then cured within the shell casting 64 and the second upper replica 48-II.

In the last step, the completed appliance 10 is removed from the mold halves 66, 68 and the second upper casting 48-II. The appliance 10 is then finished to remove burrs, foreign maetrial, and is given a buffing and is then ready for final fitting to its user.

The method of making this appliance 10 as just described is new and unique, but utilizes tools and materials that dental labs presently utilize and have expertise with. This invention is immediately suitable for commercial professional, and personal usage with the materials, techniques and dental equipment presently in place.

Although other advantages may be found and realized and various modifications may be suggested by those versed in the art, be it understood that I embody within the scope of the patent warranted hereon, all such embodiments as reasonably and properly come within the scope of my contribution to the art.

I claim as my invention:

1. An oral appliance for improving breathing during sleep, for reducing apneic events, and for reducing snoring, comprising:
   (a) a rigid structural shell
   (b) relatively pliable uprigth tooth socket means for conformably engaging upright inner and outer surfaces of a plurality of maxilla teeth;
   (c) generally generally vertical cam structure means projecting downward from a front end of said rigid structural shell for engaging and advancing the mandible structure forward with respect to the maxilla structure; and in which
   (d) said pliable tooth socket means is sufficiently soft and pliable so that it does not move a users teeth when the appliance is worn for a period of sleep, so that use of the appliance repetitively for extended periods of sleep is essentially painless.

2. The oral appliance of claim 1, in which said pliable socket means has an upper portion for engaging the upper outer gum at a level above exposed teeth.

3. The oral appliance of claim 2, in which said upper portion is at least 3 mm (0.12 inches) high.

4. The oral appliance of claim 2, including a second upper portion for engaging the upper inner gum inside of the teeth.

5. The oral appliance of claim 2, including rigid structure on the outside of said upper portion, said rigid structure being rigidly connected to said mandible pushing means.

6. The oral appliance of claim 1, in which said pliable socket means is comprised of silicone.

7. An oral appliance for improving human breathing, for reducing apneic events and for reducing snoring, comprising (a) a generally U-shaped rigid structural shell having generally concave upper and generally convex lower sides which are opposed to each other;
   (b) forward facing lower means on a front end of said lower side for engaging and advancing a mandible; and
   (c) pliable and generally upright upper means in said upper side for engaging upright maxilla structure and for positioning said shell with respect to said maxilla structure and for preventing contact between said shell and the teeth of an appliance user, said upper means being relatively soft and pliable as compared to said shell so that said appliance will not cause moving of teeth and so that said appliance may be worn in the human mouth painlessly during extended periods of sleep.

8. The oral appliance of claim 7, in which both said structural shell and said pliable means extend upward above the gum line, said pliable means having a rearward facing upper portion for engaging the upper outer gum.

9. The oral appliance of claim 8, in which said structural shell and said pliable means extend above the gum line both in front and to the rear of said lower means, said pliable means having a second portion for engaging the upper inner gum.

10. A method of painlessly improving breathing, reducing apneic events and reducing snoring, comprising the steps of
    (a) placing a rigid oral appliance shell within a users mouth and in between the users upper and lower teeth;
    (b) locating the shell in the users mouth by pliantly engaging generally upright maxilla structure with a relatively soft and pliable generally upright structure secured to said shell;
    (c) engaging and advancing the users mandible structure relatively forward with lower structure on the front of said shell; and
    (d) preventing direct contact between said rigid shell and the users upper teeth with said soft pliable structure, so that the appliance can be worn for an extended peirod of sleep without pain from the users teeth being moved by the shell.

11. The method of claim 10, including the further step of pliantly engaging the users upper outer gum.

12. The method of claim 10, including the further step of pliantly engaging upright outer surfaces of upper teeth.

13. The method of claim 10, including the further step of pliantly engaging both the inner and outer upper gums.

14. The method of claim 10, including the further step of matching a pliant said soft structure in said oral appliance to upright surfaces of the upper teeth and gums.

15. The method of claim 14, including the further steo of inserting said pliant engaging structure is said shell.

16. The method of claim 10, including the further step of backing up said soft structure with said rigid shell.

17. The method of claim 10, including the further step of pliantly enclosing upper teeth.

18. A painless oral appliance for a human, for improving breathing during sleep, for reducing snoring, and for preventing obstructive sleep apnea syndrome, comprising
    (a) a relatively rigid generally U-shaped shell having an upward facing tray with an upwardly concave cross-section, said tray having a rigid partial annular plate to be positioned below a users upper teeth, and a rigid front upright to be positioned in front of a users upper teeth;

(b) cam structure secured to and extending downward from a front of said shell, for directly engaging and advancing the users relatively rigid mandible structure; and (c) a relatively soft and pliant maxilla engaging means in the the topside of said plate and the backside of said front upright, for conformally engaging the users upper teeth and for preventing contact beteen the shell and the users teeth, so that the appliance can be worn painlessly and repetitively for extended periods of comfortable sleep by a human being who, without the appliance, would otherwise have difficulty with at least one of the group of breathing, sleep apnea, and/or snoring.

19. The oral appliance of claim 18, in which said soft and pliant structure has a soft and pliable tooth socket custom fitted to the users upper teeth.

20. The oral appliance of claim 18, in which said shell includes a rigid inner upright to be positioned inside of a users upper teeth, and in which said soft and pliant structure includes a soft and pliant inner upper structure on the front side of said inner upright to prevent contact between the inner upright and the users teeth.

* * * * *